United States Patent [19]
Cohen et al.

[11] Patent Number: 5,348,476
[45] Date of Patent: Sep. 20, 1994

[54] SYSTEM FOR FABRICATION OF DENTAL CAST POST AND CORE USING A BURN-OUT POST

[75] Inventors: Brett I. Cohen, Nanuet; Allan S. Deutsch, New York, both of N.Y.

[73] Assignee: Essential Dental Systems, Inc., South Hackensack, N.J.

[21] Appl. No.: 157,813

[22] Filed: Nov. 24, 1993

[51] Int. Cl.$^5$ ............................................. A61C 5/08
[52] U.S. Cl. ..................................... 433/220; 433/221
[58] Field of Search ............... 433/165, 220, 221, 224, 433/225, 223

[56] References Cited

U.S. PATENT DOCUMENTS

| | | | |
|---|---|---|---|
| 313,738 | 3/1885 | How | 433/221 |
| 352,855 | 11/1886 | Buttner | 433/220 |
| 553,394 | 1/1896 | Davis | 433/221 |
| 2,655,724 | 10/1953 | Brooks | 433/221 |
| 3,638,312 | 2/1972 | Szwarc et al. | |
| 3,755,897 | 9/1973 | Kurer | |
| 3,925,895 | 12/1975 | Kliment et al. | |
| 3,949,476 | 4/1976 | Kahn | |
| 4,355,978 | 10/1982 | Ericson | |
| 4,396,377 | 8/1983 | Roemer et al. | |
| 4,459,193 | 7/1984 | Ratcliffe et al. | |
| 4,602,076 | 7/1986 | Ratcliffe et al. | |
| 4,603,726 | 8/1986 | Pfannenstiel et al. | |
| 4,643,678 | 2/1987 | Hansen | |
| 4,668,712 | 5/1987 | Hino et al. | |
| 4,744,753 | 5/1988 | Ross | |
| 4,777,190 | 10/1988 | Sasaki et al. | |
| 4,820,159 | 4/1989 | Weissman | |
| 4,886,456 | 12/1989 | Ross | |
| 4,932,870 | 6/1990 | Miller | |
| 5,028,638 | 7/1992 | Heid et al. | |
| 5,037,473 | 8/1991 | Antonucci et al. | |
| 5,047,442 | 9/1991 | Sasaki et al. | |
| 5,051,092 | 9/1991 | Miller | |
| 5,147,903 | 9/1992 | Podszun et al. | |
| 5,155,252 | 10/1992 | Yamamoto et al. | |

FOREIGN PATENT DOCUMENTS

| | | | |
|---|---|---|---|
| 391683 | 5/1933 | United Kingdom | 433/221 |
| 2243783 | 11/1991 | United Kingdom | 433/225 |

*Primary Examiner*—Cary E. O'Connor
*Attorney, Agent, or Firm*—Gottlieb, Rackman & Reisman

[57] ABSTRACT

A method and system for preparing a cast post and core in a dental root canal procedure is provided. The method comprises the steps of removing the root canal material from the tooth; cutting out a post-hole in the tooth having a substantially uniform width; cutting out at least one annular tier along the hole; placing a burn-out post having at least one flange into the post-hole so that the flange is seated on the annular tier; applying an acrylic resin onto the tooth and over the burn-out post in order to form a core, and finally removing the core with the burn-out post from the tooth in order to form a casting.

17 Claims, 3 Drawing Sheets

SYSTEM FOR FABRICATION OF DENTAL CAST POST AND CORE USING A BURN-OUT POST

BACKGROUND OF THE INVENTION

This invention relates to a novel dental burn-out post, and more particularly, to a method for preparing a dental cast post and core in a dental root canal procedure.

In conventional root canal techniques, it is generally practiced to form post-holes in teeth after which a dental pre-fabricated post is placed therein. Suitable examples of pre-fabricated posts include the products FLEXI-POST and FLEXI-FLANGE, manufactured by Essential Dental Systems, Inc. of South Hackensack, N.J.

Then, the dentist or dental practitioner builds up the core in order to create an umbrella-like configuration. Conventional core materials include composites, amalgams and glass ionomer cements. The disadvantage of this system is that the post and core are constructed from two different materials. As a result, different properties (tensile strength, modular elasticity, etc.) are present. Consequently, failure between the two interfaces in the system is facilitated.

Another technique includes the formation of an umbrella and is known as a cast post system. The umbrella, comprising a plastic post and a core made from an acrylic, is sent to a dental lab and east into a precious metal. Thereafter, it is sized to the root canal and then fitted therein. Once this is done, a final crown is placed over the portion (core and shaft) which has been cast.

The above technique is directed to the use of a cast post, which remains a viable technique for many dentists and dental practitioners. To date, however, there has been no easy standardized way to achieve a reliably predictable result. In other words, prior art systems failed to provide adequate stability, reliability and ease of use. When using a cast post system, the resulting coronal portion of the tooth does not adapt properly to the final cast. As a result, a pooling of the cement can occur and retentive failure of the final cast is hastened.

Accordingly, it is desirable to provide a method for preparing a cast post and core for a dental root canal procedure which is both reliable and predictable.

SUMMARY OF THE INVENTION

Generally speaking, in accordance with the invention, a method and system for preparing a cast post and core in a dental root canal procedure is provided. The method comprises the steps of removing the root canal material from the tooth; cutting out a hole in the tooth having a substantially uniform width; cutting out at least one annular tier along the hole; and placing a burn-out post having at least one flange into the tooth hole so that the flange is seated on the annular tier; applying an acrylic resin onto the tooth and over the burn-out post in order to form a core, and finally removing the core with the burn-out post from the tooth in order to form a casting.

In practice, the plastic burn-out post of the invention is utilized in combination with a specific countersink pre-sized drill bit. The drill bit is used to cut out a post hole in the canal that is sized to receive the burn-out post therein.

The acrylic resin that is applied over the burn-out post in order to form a core is preferably of the dual cure type—the resulting cure is both light cured and chemically cured. Thus, when applying the acrylic resin to the tooth, a light cure is applied to the core end of the post to ensure that the acrylic resin has set appropriately. Thereafter, a chemical cure is achieved by a cross-linking reaction of the components of the resin when combined.

Once the setting of the core is completed, the dentist will remove the acrylic resin core and burn-out post adduct from the root canal and send it to a lab to be cast into either non-precious, semi-precious or precious metal. Then, the dentist places the casting to the root canal and cements it into place. Finally, a crown is constructed to finish the restoration process.

Accordingly, it is desirable to provide an improved method for preparing a cast post and core in a dental root canal procedure.

Another object of the invention is to provide a dental cast post and core which has improved stability and reliability.

A further object of the invention is to provide an improved dental burn-out post for use in the preparation of a dental cast post and core.

Still another object of the invention is to provide an acrylic that is suitable and the preparation of a dental cast post and core.

Other objects and advantages of the invention will impart the obvious and will impart the apparent from the following description.

The invention accordingly comprises the several steps and the relation of one or more of such steps with respect to each of the others, the system embodying the features of construction, combination of elements in arrangement of parts which are adapted to effect such steps, and the product which possesses the characteristics, properties, and relation of components, all as exemplified in the detailed disclosure hereinafter set forth, and the scope of the invention will be indicated in the claims.

BRIEF DESCRIPTION OF THE DRAWINGS

For a fuller understanding of the invention, reference is made to the following description, taken in connection with the accompanying drawings, in which.

DETAILED DESCRIPTION OF THE PREFERRED EMBODIMENT

Figure 1:
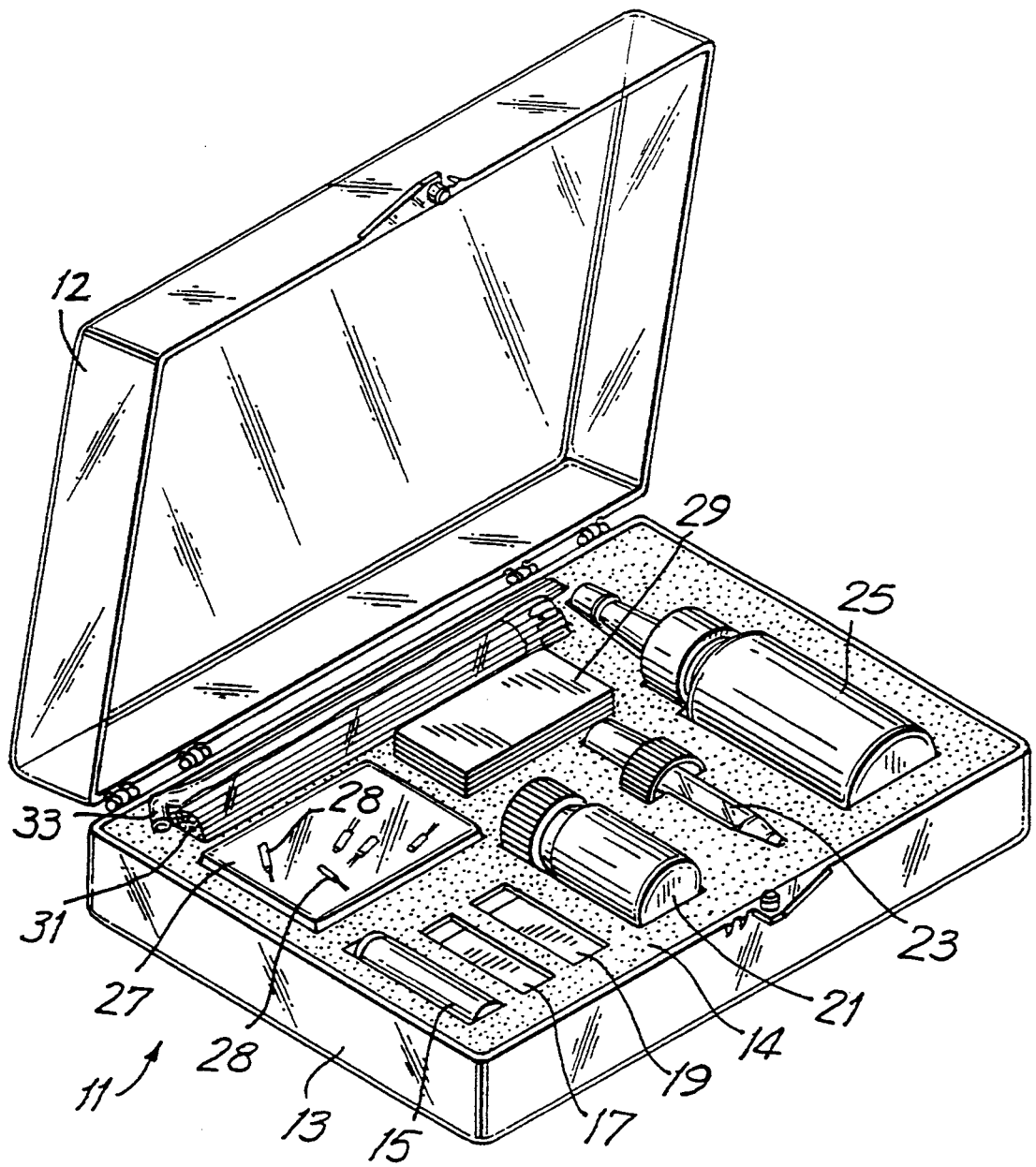
FIG. 1 is a perspective view illustrating a kit for retaining the various components of the inventive system.

Referring first to FIG. 1, a kit generally indicated at 11, and used for retaining the various components of the inventive dental cast post and core fabrication system, is described. Kit 11 includes a base 13 and a hinged clear plastic cover 12. Base 13 houses a plastic form 14 that defines a series of compartments for retaining the various components of the system.

As shown in FIG. 1, the lower right portion of form 14 includes a first compartment for retaining a cylindrical container 15 and two additional compartments for retaining a pair of rectangular containers 17 and 19. Cylindrical container 15 contains a primary reamer and a countersink drill bit, as described in greater detail below, which are used in preparing a post-hole in a tooth. Container 17 includes a plurality of burn-out posts, made in accordance with the invention, while container 19 includes a plurality of similarly shaped or configured brass temporary posts.

Continuing with FIG. 1, form 14 includes additional compartments for retaining a jar 21, an eye dropper 23, a bottle 25, a series of pads 29, and a plastic receptacle 27 containing application brushes 28. Jar 21 and bottle 25 contain respectively the liquid and powder components of the acrylic cement of the invention. Eye dropper 23 is used to apply the liquid component to one of the mixing pads 29 where it is mixed with the powdered component using one of the application brushes 28 (or a plastic spatula 31) in order to form the acrylic resin cement composition of the invention, as described in greater detail hereinafter.

As further shown in FIG. 1, kit 11 also houses a series of mixing spatulas 31 which are used to mix the acrylic resin, as described above. Finally, kit 11 includes a holder 33, which is used for holding application brushes 28 when mixing the powder and liquid components.

Kit 11 is typically sent by the dental manufacturer to the dental practitioner along with instructions for carrying out the inventive method of fabricating a dental cast post and core using a burn-out post, as described below.

In accordance with the invention, post-hole preparation begins with the removal of root filling material from the tooth by using a dental drill or reamer as is well known in the art. Then, in sequence, a non-end cutting drill is used until 100% of the post-hole length and 90% of the post-hole width have been prepared in the tooth.

Figure 2:
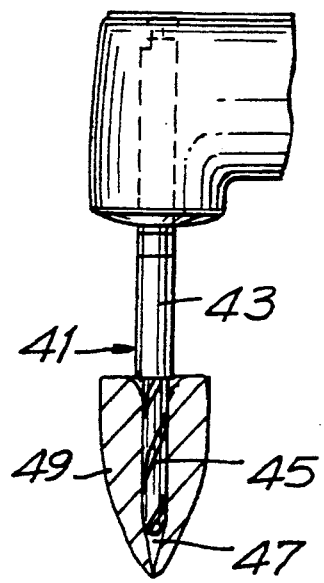
FIG. 2 is a front elevational view illustrating the use of a primary reamer in order to prepare the post-hole in the tooth.

When 100% of the post-hole length and 90% of the width have been prepared, in accordance with the invention, an appropriate primary reamer 41 is used, as illustrated in FIG. 2. Primary reamer 41 comprises a rotating shaft 43 which is retained in a conventional dental drill and a bit portion 45. Primary reamer 41 is drilled into post-hole 47 of tooth 49 in order to widen the post-hole. In use, it is preferred to lubricate the canal of tooth 49 with either water, an anesthetic solution or some other type of suitable wetting agent, in order to eliminate cutting friction.

Figure 3:
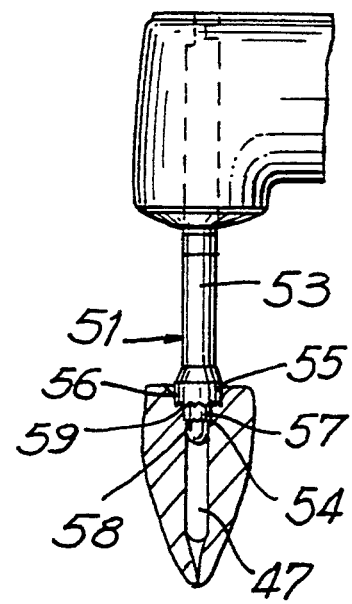
FIG. 3 is a front elevational view illustrating the use the countersink drill bit of the invention to prepare the post-hole for reception of the burn-out post.

Turning now to FIG. 3, a countersink drill bit 51 in accordance with the invention is now used to further prepare post-hole 47 formed in tooth 49. Countersink drill bit 51 comprises an extending shaft 53 that is retained in a dental drill, a first head 55, and a second head 57. First head 55 has a diameter which is larger than the diameter of shaft 53 and includes a plurality of annularly spaced projecting teeth 59. Second head 57 has a width which is wider than the width of shaft 53, but which is narrower than the width of head 55. Head 57 also includes a plurality of annularly spaced projecting teeth 58.

In use, countersink drill bit 51 cuts a series of preparations in the root canal. Specifically, first head 55 drills out a primary tier 56 within the post-hole 47 and secondary head 57 drills out a second tier 54 within post-hole 47. Tiers 56 and 54 are used for seating the flange members of the burn-out post of the invention in the root canal hole, as described below.

Figure 4:
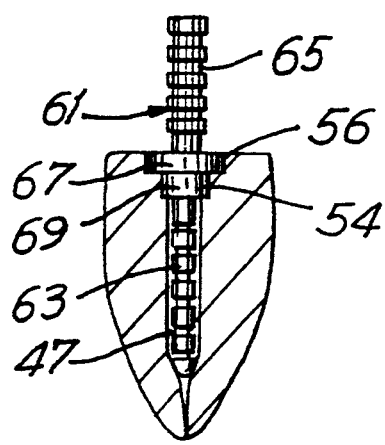
FIG. 4 is a front elevational view showing the burn-out post of the invention being inserted into the post-hole.

Turning now to FIG. 4, a burn-out post 61 is first selected in size to match the size of the post-hole prepared by countersink drill bit 51, and then placed into post-hole 47. Burn-out post 61 is made of a suitable low temperature melting plastic, as is well known in the art. Burn-out post 61 comprises a shaft 63 adapted to be received inside the post-hole, and a stem 65 extending upwardly from the shaft and adapted to sit above the tooth. The shaft 63 has a ribbed configuration so that, during final cementation of the cast, as described below, the cement can adhesively interlock with the final cast post. Stem 65 has a ribbed configuration in order to enable the acrylic resin to adhesively interlock, as is well known in the art.

Burn-out post 61 also includes a pair of flanges 67 and 69 located between shaft 63 and stem 65. First flange 67 has a larger diameter and is adapted to be seated along primary tier 56 formed in the post-hole. Second flange 69 has a smaller diameter and is adapted to be seated along secondary tier 54 formed in post-hole 47 and below primary tier 56.

Figure 5:
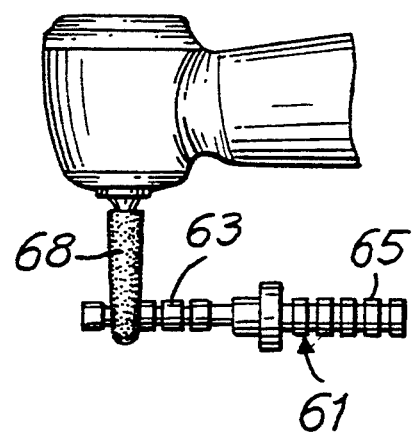
FIG. 5 is a front elevational view illustrating how the shaft of the burn-out post is shortened to achieve complete seating of the burn-out post in the post-hole.

If flanges 67 and 69 are not fully seated in post-hole 47, the dental practitioner preferably removes burn-out post 61 from the root canal, as shown is FIG. 5, and then shortens shaft 63 at its apical end. This is accomplished by utilizing a burr 68 or some other type of standardized cutting tool so that shaft 63 has a length that is desired. Once the desired length of shaft 63 is achieved, burn-out post 61 is placed once again into post-hole 47, as shown in FIG. 4.

Figure 6:
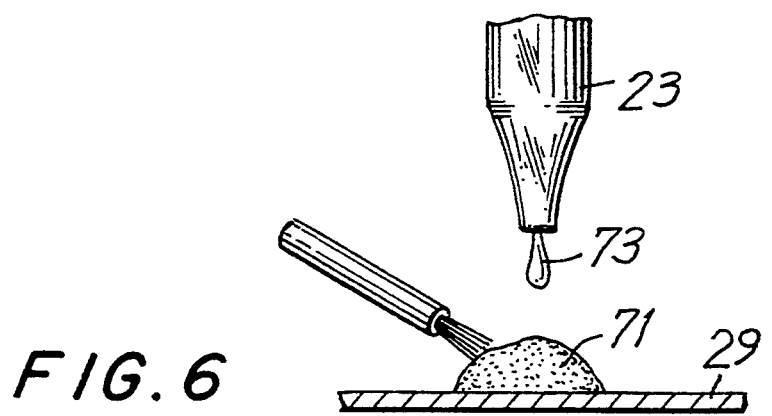
FIG. 6 is a front elevational view showing the mixing of the powder and liquid components of the acrylic resin.
Figure 7:
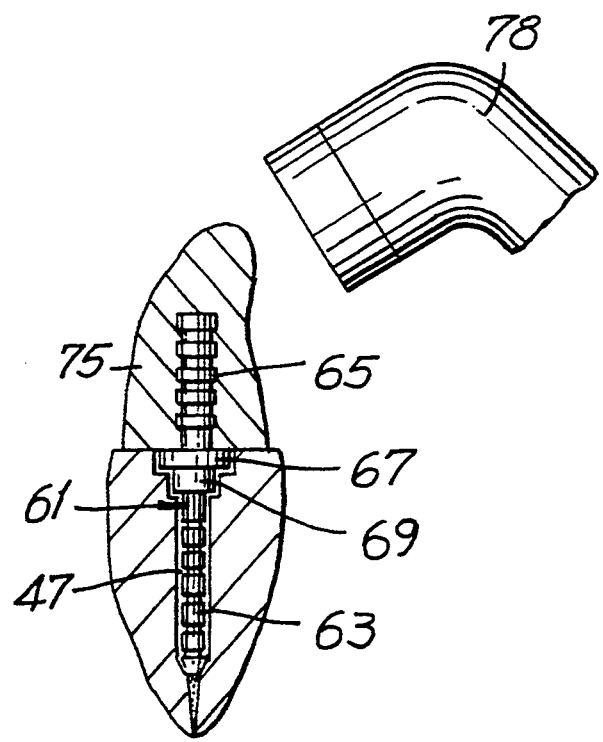
FIG. 7 is a front elevational view in partial cross-section showing application of a curing light and the formation of the acrylic resin core that is attached to the burn-out post of the invention.

Reference is now made to FIGS. 6 and 7, which describe application of a resin composition over burn-out post 61 in order to form a core. In accordance with the invention, the resin is preferably a dual cure acrylic that is prepared from combining a powdered ingredient 71 and a liquid ingredient 73.

In particular, the dental practitioner takes a selected amount of powdered ingredient 71 from bottle 25 (see FIG. 1) and places it on one of pads 29. Then, a selected amount of liquid ingredient 73 is taken from jar 21 (see FIG. 1) and dispensed onto powdered ingredient 71 by means of dropper 23. Thereafter, the two ingredients are mixed by means of one of application brushes 28 or mixing spatula 31 in order to form the resin composition.

Once the resin composition is prepared, as shown in FIG. 7, it is used to build up incrementally a core 75 over burn-out post 61. Simultaneously and selectively, the dental practitioner applies a blue light source by means of a visible light curing apparatus 78 for curing purposes, as is well known in the art. In accordance with the invention, in order to cure the resin sufficiently to prevent slumping, an approximately 10-second blue light exposure is desired before adding additional resin as part of the next increment. Once core 75 is substantially formed, one or more exposures of approximately 10 seconds of blue light from either side of core 75 is sufficient to cause the final cure. Simultaneously, a chemical cure of core 75 takes place by a cross-linking reaction between the two resin components (powder and liquid) once they are mixed.

Once the core is fully formed, burn-out post 61 plus resin core 75 is removed from post-hole 47, and the post portion is blue light cured to make sure that all of the resin has set. The final adduct is then sent to a laboratory to be cast into either non-precious, semi-precious, or precious metal, as is well known in the art.

While the adduct is being cast, a brass temporary post from kit 11, and having the same configuration as burn-out post 61, is placed into the root canal of the patient. Then, a transparent or translucent crown is filled with the resin material, which is blue light cured for about 30 seconds, resulting in a dental temporary. The purpose of the brass temporary post is to provide a substructure for attaching the temporary crown.

Figure 8:
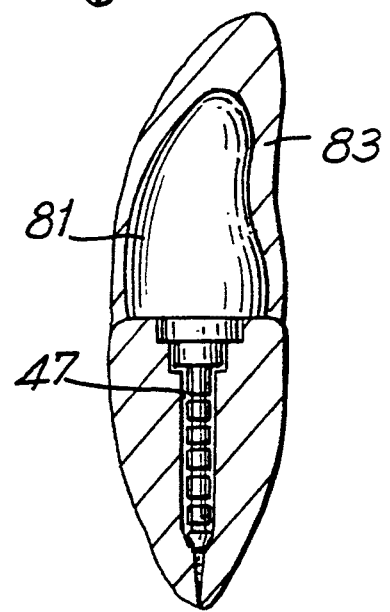
FIG. 8 is a front elevational view in partial cross-section illustrating the application of the final burn-out adduct cast with the cemented final crown.

Once the post adduct has been formed into a casting, the dental practitioner, after removing the dental temporary, tailors the final casting to the root canal. Specifically, as shown in FIG. 8, the practitioner trial seats a finished casting 81 in order to make sure that it is properly seated in the root canal. Then, final cement is placed into post-hole 47 and along the post of the casting, after which the entire casting is appropriately seated in place on the tooth and within post-hole 47. Finally, a crown is constructed, indicated at 83, as is well known in the art, in order to finish the restoration process.

Attention is now directed to the dental resin composition that is used in the inventive process.

The dental resin composition of the invention includes a polymer matrix in an amount between about 30 and 90 weight percent based on the overall weight of the composition. Preferably, the polymer matrix comprises an epoxy matrix, and even more preferably an acrylic matrix. The acrylic matrix is formed from monomers and polymers of acrylates and methacrylates, such as mono-, di-, tri- and tetracrylates and methacrylates.

Suitable monomers of monoacrylates include methylmethacrylate, ethylmethacrylate, butylmethacrylate, propylmethacrylate, and phenylmethacrylate. The preferred monomer is butylmethacrylate.

Suitable monomers of diacrylates include ethylene glycol diacrylate, diethylene glycol diacrylate, 1,4-dimethylolcyclohexane diacrylate and $C_2-C_{12}$ alkylene diacrylates.

Suitable monomers of dimethacrylate include bisphenol A-glycidyl methacrylate (BIS-GMA), triethylene glycol dimethacrylate, tetraethylene glycol dimethacrylate, ethylene glycol dimethacrylate, diethylene glycol dimethacrylate, butanediol dimethacrylate, hexanedioethylene dimethacrylate, neopentylglycol dimethacrylate, isobisphenol A-glycidyl methacrylate, trimethylolpropane dimethylacrylate, bisphenol A-ethoxylated dimethacrylate and bisphenol A-dimethacrylate. The preferred monomer of dimethacrylate is bisphenol A-glycidylmethacrylate (BIS-GMA) and is present in an amount between about 5 and 75 weight percent based on the total weight of the resin composition.

Suitable monomers of triacrylates and trimethacrylates include trimethylolpropane triacrylate, tetramethylolmethane triacrylate, tetramethylolmethane trimethylacrylate, trimethylolethane trimethacrylate and trimethylolpropane trimethacrylate.

Suitable monomers of tetracrylates and tetramethacrylates include tetramethylolmethane tetracrylate and tetramethylolmethane tetramethacrylate.

Other suitable monomers include styrene and vinyl acetate monomers.

Suitable polymers (fillers) of methacrylates include polymethylmethacrylate, polyethylmethacrylate, polybutylmethacrylate, polypropylmethacrylate, and polyphenylmethacrylate.

Other suitable polymers include polystyrene and poly(vinyl acetate).

The purpose of the polymer matrix, specifically the acrylic matrix formed from monomers and polymers of acrylates and methacrylates, is to provide a binding network, thereby providing strength to the composite resin composition.

In order to prepare the composite resin composition, a catalyst (powder) component and a base (liquid) component are mixed together, which causes a chemical setting reaction. Particularly, the catalyst component includes a catalyst or polymerization initiator in an amount between about 0.2 and 10 weight percent, and at least one epoxy monomer or polymer in an amount between 15 and 95 weight percent.

The catalyst of the catalyst component is typically a free radical source, and more preferably an organic peroxide or ketone. Suitable organic peroxides or ketones include benzoyl peroxide, acetyl peroxide, parachlorobenzoyl peroxide, cumyl peroxide, t-butyl peroxide, lauroyl peroxide, t-butyl hydroperoxide, methylethyl ketone peroxides, t-butyl peroxybenzoate, 2,5-dimetylhexane, 2,5-dihydroperoxide, t-cumyl hydroperoxide and camphorquinone. Benzoyl peroxide is the most preferred catalyst for the catalyst component.

The base component which is used for preparing the composite resin cement composition includes a base or accelerator in an amount between about 0.2 and 10 weight percent, and at least one epoxy monomer or polymer in an amount between about 15 and 95 weight percent. Preferably, the base of the base component is an amine compound chosen from amines such as propylamine, N-butylamine, pentylamine, hexylamine, dimethylamine, diethylamine, dipropylamine, di-n-butylamine, dipentylamine, trimethylamine, triethylamine, tripropylamine, tri-n-butylamine, tripentylamine, 4-methylaniline, N-N-bis-(2-hydroxyethyl)-3,5-dimethylaniline, N-methyl-N(2-hydroxyethyl)-4-methylaniline and long chain fatty amines such as NN' dimethylaniline and N-methyldiphenylamine. Diamines can also be used such as ethylene diamine, trimethylene diamine, tetramethylene diamine, pentamethylene diamine and hexamethylene diamine.

As will be shown in the examples hereinbelow, the preferred amine is N,N-dimethyl-p-toluidine. Other toluidines may be used such as NN' dihydroxyethyl-p-toluidine and N,N-diethyl-p-toluidine.

For the base component, the epoxy monomer is chosen preferably from monomers of methacrylate, as described hereinabove.

When the catalyst and base components are combined, a chemical setting reaction takes place which will last on the average of 4 to 7 minutes.

Preferably, substantially equal amounts of catalyst component and base component are combined in order to form the inventive composite resin cement composition. Once the catalyst and base components are combined, the peroxide compound contained in the catalyst component is fully initiated when brought into contact with the amine compound (free radicals are formed) found in the base component. As a result, substantial polymerization of the acrylic monomers and polymers takes place, resulting in a strong polymer matrix of the composite resin composition.

Other ingredients, such as stabilizers and absorbents, may be present to increase shelf life and prevent degradation of properties. Also, various dyes or pigments may be added to obtain various color shades for conforming to the tooth color to which the composition is applied.

The resin composition used in the invention may be colored with a metal oxide. Suitable metals for the metal oxide include titanium (producing a white colored oxide), iron (producing either a red or black colored oxide), cadmium or iron (producing a yellow colored oxide) and chromium or iron (producing a brown colored oxide). Any combination may be used to produce a variety of tooth color shades. The metal oxide colorants may be added in an amount between about 0.005 and 0.5 weight percent.

In order to better comprehend the resin cement composition, the following examples are provided. In each example, a substantially equal amount of the base and catalyst components were mixed for approximately 30 seconds in order to initiate a chemical setting reaction.

EXAMPLE 1

| Catalyst (Powder) Formulation | |
| --- | --- |
| Polyethylmethacrylate | 96.4 weight percent (96.4 grams) |
| Titanium dioxide | 0.2 weight percent (0.2 grams) |
| Cadmium pigment | 0.4 weight percent (0.4 grams) |
| Benzoyl peroxide | 3.0 weight percent (3.0 grams) |
| Base (Liquid) Formulation | |
| BIS-GMA | 65.8 weight percent (65.8 grams) |
| Camphorquinone | 0.13 weight percent (.13 grams) |
| N,N-dimethyl-p-toluidine | 0.86 weight percent (0.86 gram) |
| Butylmethacrylate | 34.0 weight percent (34.0 grams) |

In order to prepare the catalyst components, 96.4 grams of polyethylmethacrylate and 3 grams of benzoyl peroxide were mixed together. Then, titanium dioxide (0.2 gram) and cadmium pigments (0.4 gram) were blended together, stirred and then added to the resulting mixture. This resulted in approximately 100 grams of the catalyst component portion of the composition.

In order to prepare the base component, 34 grams of butylmethacrylate and 0.86 grams of N,N-dimethyl-p-toluidine were mixed together until a homogenous solution resulted. Then, 65.8 grams of warm BIS-GMA were added to the above solution. Then, camphorquinone (0.13 grams) was mixed with the BIS-GMA resin solution that was mixed before and approximately 100 grams of the base portion of the composition was obtained.

EXAMPLE 2

| Catalyst (Powder) Formulation | |
| --- | --- |
| Polymethylmethacrylate | 95.0 weight percent (95.0 grams) |
| Titanium dioxide | 4.5 weight percent (4.5 grams) |
| Benzoyl peroxide | 0.5 weight percent (0.5 gram) |
| Base (Liquid) Formulation | |
| BIS-GMA | 50 weight percent (50 grams) |
| Camphorquinone | 0.2 weight percent (0.2 gram) |
| Methylmethacrylate | 48.8 weight percent (48.80 grams) |
| N,N-dimethyl-p-toluidine | 1.0 weight percent (1.0 grams) |

Both the catalyst and base components are prepared from the above ingredients in the same manner as in Example 1.

EXAMPLE 3

| Catalyst (Powder) Formulation | |
| --- | --- |
| Polypropylmethacrylate | 80.0 weight percent (80 grams) |
| Polystyrene | 15.0 weight percent (15.0 grams) |
| Titanium dioxide | 2.0 weight percent (2.0 grams) |
| Benzoyl peroxide | 3.0 weight percent (3.0 grams) |
| Base (Liquid) Formulation | |
| BIS-GMA | 48.5 weight percent (48.5 grams) |
| Ethylmethacrylate | 30 weight percent (30 grams) |
| Butylmethacrylate | 20 weight percent (20 grams) |
| Camphorquinone | 0.5 weight percent (0.5 gram) |
| N,N-dimethyl-p-toluidine | 1.0 weight percent (1.0 grams) |

Both the catalyst and base components are prepared from the above ingredients in the same manner as in Example 1.

EXAMPLE 4

| Catalyst (Powder) Formulation | |
| --- | --- |
| Polyethylmethacrylate | 98.0 weight percent (98.0 grams) |
| Iron Oxide | 0.02 weight percent (0.02 gram) |
| Benoxyl Peroxide | 1.8 weight percent (1.8 grams) |
| Base (Liquid) Formulation | |
| BIS-GMA | 10.0 weight percent (10.0 grams) |
| Methylmethacrylate | 43.5 weight percent (43.5 grams) |
| Butylmethacrylate | 45.0 weight percent (45.0 grams) |
| N,N-dimethyl-p-toluidine | 1.0 weight percent (1.0 grams) |
| Camphorquinone | 0.5 weight percent (0.5 gram) |

Both the catalyst and base components are prepared from the above ingredients in the same manner as in Example 1.

The system described herein is advantageous because it is dual cured and results in an aesthetic and a strong acrylic matrix system.

Moreover, because the burn-out post of the system includes at least one flange which sits on at least one tier in the post-hole, there is maximum metal to dentin contact when the cast is in place. As a result, a pooling of cement is not present, and the risk of fatigue or failure is inhibited.

It will thus be seen that the objects set forth above, among those made apparent from the preceding description, are efficiently attained and, since certain changes may be made in carrying out the above process and the described products, and in the construction set forth without departing from the spirit and scope of the invention, it is intended that all matter contained in the above description and shown in the accompanying drawings shall be interpreted as illustrated and not in a limiting sense.

It is also to be understood the following claims are intended to cover all of the generic and specific features of the invention herein described and all statements of the scope of the invention, which as a matter of language, might be said to fall there between.

Particularly, it is to be understood that in said claims, ingredients or compounds recited in the singular are intended to include compatible mixtures of such ingredients wherever the sense permits.

We claim:

1. A method for preparing a post and core adduct in a dental root canal procedure comprising:
   removing root canal filling material from the tooth;
   cutting out a post-hole in said tooth having a substantially uniform width along the length thereof;
   cutting out at least one annular tier along said hole at a selected axial location;
   placing a burn-out post having at least one flange into said tooth hole such that said at least one flange is seated on said at least one annular tier;
   applying a resin composition onto said tooth and over said burn-out post in order to form a core; and
   removing the core with the burn-out post from the tooth in order to form a casting.

2. , The method of claim 1, wherein said tier cutting out step comprises cutting out a primary tier within said post-hole and a secondary tier within said post-hole.

3. The method of claim 2, wherein said burn-out post includes a primary flange that is seated on the primary tier of said hole and a secondary flange that is seated on the secondary tier of said hole.

4. The method of claim 1, wherein said resin composition comprises an acrylic composition.

5. The method of claim 4, wherein said acrylic composition is light and chemically cured once applied to said tooth and over said burn-out post.

6. The method of claim 5, further including the step of mixing a catalyst component and a base component for preparing said acrylic resin prior to said application step.

7. The method of claim 1, further including the step of placing the casting into the post-hole and over the tooth.

8. The method of claim 1, further including the step of placing a temporary post in the post-hole after said removing step, and removing said temporary post prior to said casting placement step.

9. A burn-out post used in a dental root canal procedure comprising:
   a shaft adapted to be selectively received inside a post hole formed in a tooth;
   a stem extending from said shaft and adapted for disposition above said tooth;
   a primary flange adapted to be seated on a primary tier formed along said post hole and a secondary flange adapted to be seated on a secondary tier formed along said post hole, said primary and secondary flanges being located between said shaft and said stem.

10. The post of claim 9, wherein the primary flange has a diameter greater than the diameter of the secondary flange.

11. The post of claim 10, wherein the primary flange is disposed above said secondary flange.

12. A system for preparing a core and post adduct in a dental root canal procedure comprising:
    a countersink drill bit having at least one head and adapted to be used in cutting out a post-hole having at least one tier in a tooth;
    a burn-out post comprising a depending shaft and an extending stem and at least one flange located between said shaft and said stem with a diameter larger than the diameter of the shaft, said post adapted to be received in said cut-out post-hole with said at least one flange seated along said at least one tier; and
    a resin composition suitable for application to said burn-out post when received in said post-hole in order to form a post and core adduct.

13. The system of claim 12, wherein said drill bit has a pair of heads for cutting out a first tier and a second tier.

14. The system of claim 13, wherein said burn-out post includes a primary flange and a secondary flange suitable for seating respectively along said first tier and said second tier.

15. The system of claim 14, wherein the primary flange has a diameter greater than the diameter of the secondary flange.

16. The system of claim 15, wherein the primary flange is disposed above said secondary flange.

17. The system of claim 16, wherein said resin composition is prepared from a catalyst component and a base component.

* * * * *